US00PP25003P3

(12) United States Plant Patent
Olesen

(10) Patent No.: US PP25,003 P3
(45) Date of Patent: Oct. 28, 2014

(54) ROSE PLANT NAMED 'POULTC013'

(50) Latin Name: ***Rosa* hybrid**
Varietal Denomination: Poultc013

(75) Inventor: Mogens Nyegaard Olesen, Fredensborg (DK)

(73) Assignee: Poulsen Roser A/S, Fredensburg (DK)

( * ) Notice: Subject to any disclaimer, the term of this patent is extended or adjusted under 35 U.S.C. 154(b) by 96 days.

(21) Appl. No.: 13/507,039

(22) Filed: May 31, 2012

(65) Prior Publication Data

US 2013/0326738 P1 Dec. 5, 2013

(51) Int. Cl.
*A01H 5/00* (2006.01)

(52) U.S. Cl.
USPC ..... Plt./104

(58) Field of Classification Search
USPC ..... Plt./104
See application file for complete search history.

(56) References Cited

PUBLICATIONS

UPOV ROM PLUTO Database Citation for 'Poultc013' Apr. 2, 2013.*

* cited by examiner

*Primary Examiner* — Wendy C Haas

(57) ABSTRACT

A new garden rose plant of the Ground Cover class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poultc013'.

SUMMARY OF THE INVENTION

The present invention constitutes a new and distinct variety of garden rose plant which originated from a controlled crossing between the female unpatented seed parent, an unnamed seedling, and the male unpatented pollen parent, also an unnamed seedling.

The two parents were crossed during the summer of 2002 and the resulting seeds were planted in a controlled environment in Fredensborg, Denmark. The new variety, named 'Poultc013', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poultc013' from all other varieties of which we are aware.

As part of the rose development program, Mogens N. Olesen germinated the seeds from the aforementioned hybridization during winter of 2002 and conducted evaluations on the resulting seedlings in a controlled environment in Fredensborg, Denmark. 'Poultc013' was selected in the spring of 2003 by the inventor as a single plant from the progeny of the aforementioned hybridization.

Asexual reproduction of 'Poultc013' by traditional budding and rooted cuttings was first done by Mogens N. Olesen in the nursery in Fredensborg, Denmark in July, 2003. This initial and other subsequent asexual propagations conducted in controlled environments have demonstrated that the characteristics of 'Poultc013' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poultc013'. Specifically illustrated in the drawings are flowers at various stages of development, flower in parts, leaves, and stems, clusters of flower buds on the branch.

DETAILED DESCRIPTION OF THE VARIETY

Figure 1:
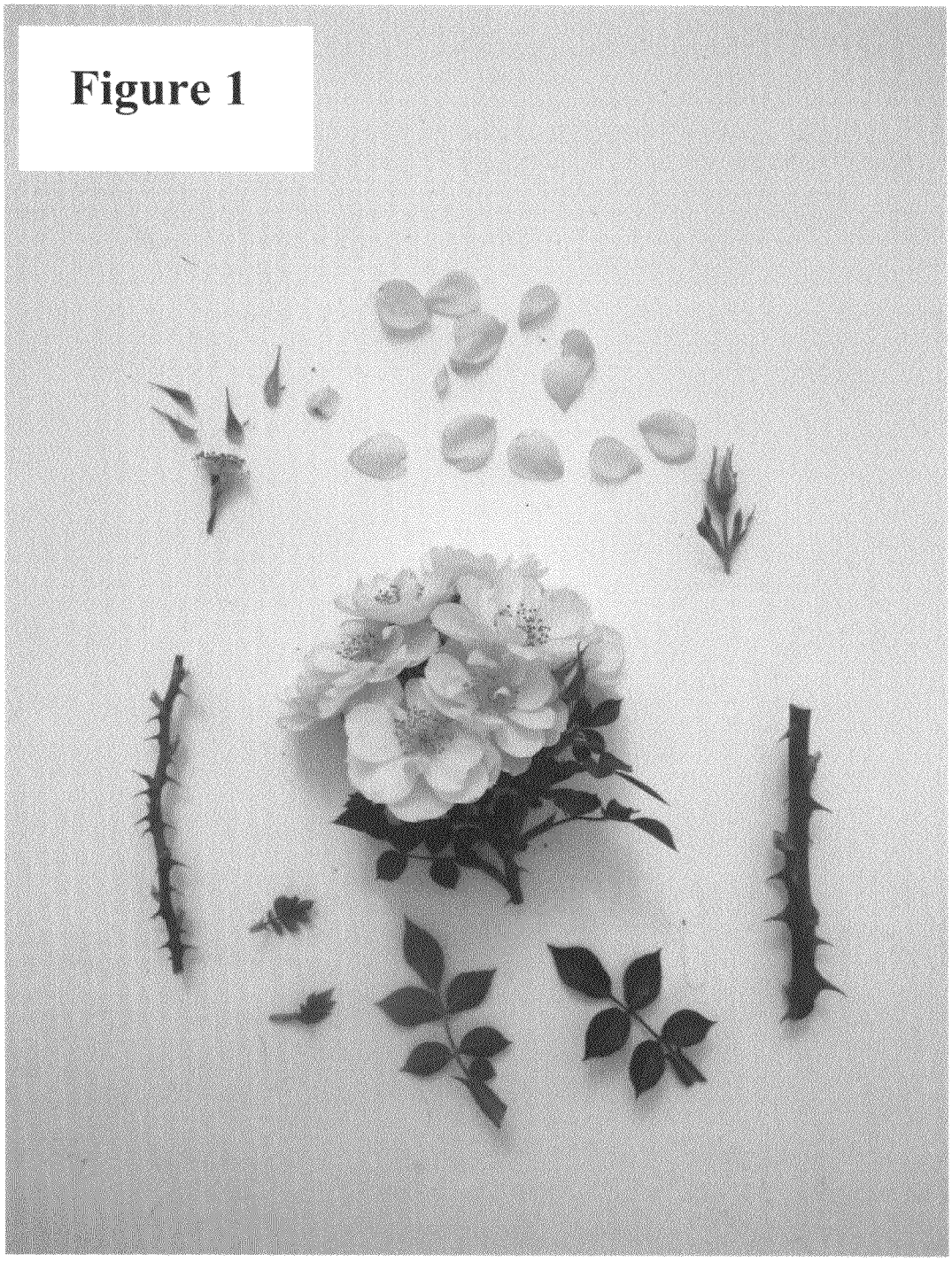
Figure 2:
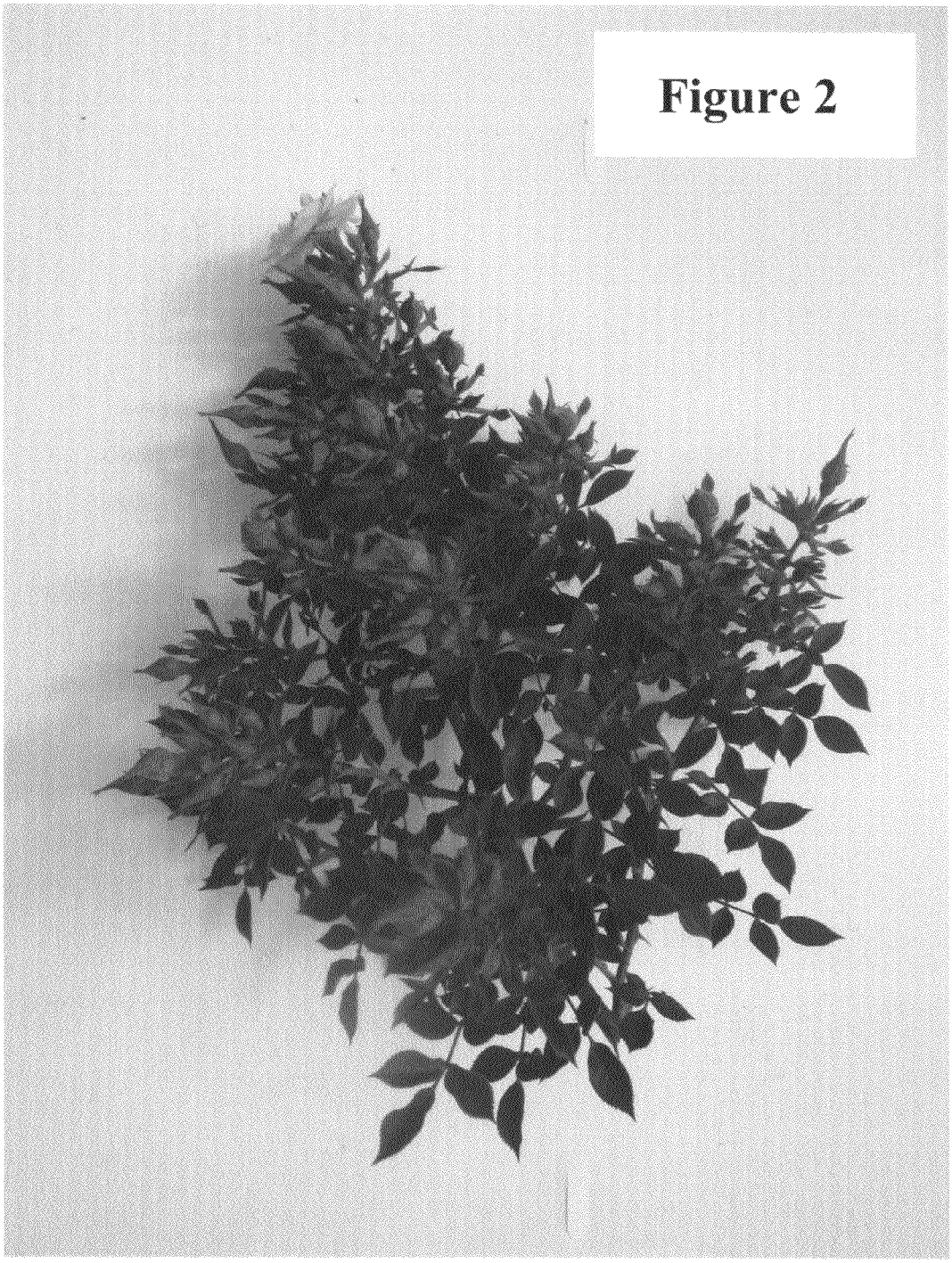

The following is a description of 'Poultc013', as observed in its growth in in a field nursery in Bakersfield, Calif. 2 years of age, and were grown on their own roots. Color references are made using The Royal Horticultural Society (London, England) Colour Chart, 2001, except where common terms of color are used.

For a comparison, several physical characteristics of the rose variety 'Poulurt', U.S. Plant Pat. No. 9,637 are compared to 'Poultc013' in Chart 1.

CHART 1

| | 'Poultc013' | 'Poulurt' |
|---|---|---|
| Petal Count | 17 | 14 to 18 |
| Flower Diameter | 45 mm | 45 mm |

CHART 1-continued

| | 'Poultc013' | 'Poulurt' |
|---|---|---|
| General Tonality of Flower Color | Yellow Group 8C | Yellow Group 6A |

FLOWER AND FLOWER BUD

Blooming habit: Continuous.

Flower bud:

*Size*.—Upon opening, 16 mm in length from base of receptacle to end of bud. Bud diameter is 6 mm.

*Bud form*.—Ovoid.

*Bud color*.—As sepals divide Yellow Group 10B.

*Sepal inner surface*.—Color: Green Group 138B. Surface: Smooth.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—20 mm long by 4 mm wide.

*Receptacle*.—Texture: Smooth. Size: 5 mm in height by 5 mm wide. Color: Yellow-Green Group 144A. Anthocyanic pigments the color of Greyed-Red Group 180A observed. Shape: Campanulate.

*Pedicel*.—Surface: Smooth. Length: 20 to 15 mm. Diameter: 1 mm on average. Color: Yellow-Green Group 144A with anthocyanic pigments the color of Greyed-Red Group 180A observed. Strength: Weak.

*Peduncle*.—Length: 3 to 10 cm. Diameter: 2 mm. Color: Yellow-Green Group 144A.

Flower bud development: Flower buds are borne in clusters of 60 to 90 flower buds per stem, resembling a panicle.

Flower bloom:

*Fragrance*.—None.

*Duration*.—The blooms have a duration on the plant of approximately 10 days. Petals fall cleanly away from plant after flowers have fully matured.

*Size*.—Flower diameter is 45 mm when open. Flower depth is 11 mm.

*Flower shape*.—General shape is an open cup.

*Shape of flower, side view*.—The upper portion is a flattened convex. The lower portion is flat.

Petalage: Under normal conditions, flowers have 17 petals total, 1 or 2 of which are petaloids.

General tonality of flower: Open flowers are Yellow Group 8C.

Petal color:

*Upon opening, after opening, outer petals and inner petals*.—Upper surface: Yellow Group 8C. Lower surface: Yellow Group 8C.

Petals:

*Petal reflex*.—None.

*Margin*.—Entire and uniform.

*Shape*.—Generally narrow elliptic. Apex shape: Rounded. Base shape: Acute.

*Size*.—21 mm (l)×15 mm (w).

*Texture*.—Smooth.

*Thickness*.—Average.

Petaloids:

*Size*.—10 mm (l) by 15 mm (w).

*Quantity*.—1 or 2.

*Shape*.—Narrow elliptic. Base is acute and the apex is round.

*Color*.—Yellow Group 8C.

Reproductive organs:

*Pollen*.—None observed.

*Anthers*.—Size: 1 mm in length. Color: Greyed-Orange Group N167A. Quantity: 30 on average.

*Filaments*.—Color: Yellow Group 12A. Length: 5 mm.

*Pistils*.—Length: 3 mm. Quantity: 15 on average.

*Stigmas*.—Color: Greyed-Yellow Group 160A.

*Styles*.—Color: Orange-Red Group 34C.

*Location of stigmas*.—Inferior in location relative to the length of the filaments and the height of the anthers.

*Hips*.—None Observed.

PLANT

Plant growth: Low growing and bushy. Plants are 30 cm in height, and 30 cm wide.

Stems:

*Color*.—Juvenile growth: Yellow-Green Group 144B. Mature growth: Yellow-Green Group 144A.

*Length*.—Canes are 15 to 20 cm from the base of the plant to the flowering portion.

*Diameter*.—6 mm.

*Internodes*.—On mature canes, there is an average distance of 20 mm between nodes.

*Surface texture*.—Young wood: Smooth. Older wood: Smooth.

Long prickles:

*Incidence*.—13 prickles per 10 cm of stem.

*Size*.—Average length of prickles on mature stems is 10 mm.

*Shape*.—Upper portion is linear. Lower portion is deep concave.

*Color*.—Juvenile prickles: Yellow-Green Group 144D with Greyed-Red Group 178B. Mature prickles: Greyed-Red Group 178A.

Plant foliage:

*Compound leaf*.—75 mm (l)×40 (w).

*Quantity*.—4 leaves per 10 cm of stem on average.

*Leaf bearing angle to the stem*.—45 degrees.

*Color of juvenile foliage*.—Upper side: Yellow-Green Group 147A. Lower side: Yellow-Green Group 147B.

*Color of mature foliage*.—Upper side: Yellow-Green Group 147A. Lower side: Yellow-Green Group 147B.

Plant leaves and leaflets:

*Stipules*.—Size: 18 mm in length. Quantity: 2 per compound leaf. Shape: Linear, slightly broad based with outward extending apecies. Margins: Finely serrated. Color: Yellow-Green Group 144A.

*Petiole*.—Length: 20 mm. Diameter: 2 mm.

*Upper surface*.—Color: Yellow-Green Group 144A.

*Lower surface*.—Color: Yellow-Green Group 144B.

*Rachis*.—Length: 30 mm. Upper surface: Color: Yellow-Green Group 144A.

*Lower surface*.—Color: Yellow-Green Group 144B.

*Leaflet*.—Quantity: Normal number of leaflets leaves in middle of the stem is 5 to 7 leaflets. Margins: Serrated. Size: Average size of the terminal leaflet on normal leaves is 20 mm in length by 11 mm wide. Shape: Generally elliptical. Base: Rounded. Apex: Aristate.

*Texture*.—Smooth.

*Thickness*.—Average.

*Arrangement*.—Odd pinnate.

*Venation*.—Reticulate.

*Glossiness*.—Very glossy.

Disease resistance: Above average resistance to powdery mildew *Sphaerotheca pannosa,* downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the ground cover rose class named 'Poultc013', substantially as illustrated and described herein, due to its abundant yellow flowers, disease resistance, and extended period of bloom.

* * * * *